United States Patent
Fiss Hobart et al.

(10) Patent No.: US 12,344,905 B2
(45) Date of Patent: Jul. 1, 2025

(54) **COMPOSITIONS AND METHODS FOR DETECTION OF *CANDIDA AURIS***

(71) Applicant: Roche Molecular Systems, Inc., Pleasanton, CA (US)

(72) Inventors: Ellen H. Fiss Hobart, Albany, CA (US); Jody Harris, Lafayette, CA (US); Andrew T. Hill, Livermore, CA (US); Jingtao Sun, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 977 days.

(21) Appl. No.: 17/311,442

(22) PCT Filed: Dec. 3, 2019

(86) PCT No.: PCT/EP2019/083389
§ 371 (c)(1),
(2) Date: Jun. 7, 2021

(87) PCT Pub. No.: WO2020/114998
PCT Pub. Date: Jun. 11, 2020

(65) Prior Publication Data
US 2022/0017973 A1 Jan. 20, 2022

Related U.S. Application Data (60) Provisional application No. 62/774,742, filed on Dec. 3, 2018.

(51) Int. Cl.
*C12Q 1/6895* (2018.01)
(52) U.S. Cl.
CPC .................. *C12Q 1/6895* (2013.01)
(58) Field of Classification Search
None
See application file for complete search history.

(56) References Cited

U.S. PATENT DOCUMENTS

| | | | |
|---|---|---|---|
| 6,773,882 B2 * | 8/2004 | Hogan | C12Q 1/6895 435/6.15 |
| 2017/0369952 A1 | 12/2017 | Hooper et al. | |
| 2018/0073086 A1 | 3/2018 | Hooper et al. | |

FOREIGN PATENT DOCUMENTS

| | | |
|---|---|---|
| EP | 3257951 A2 | 12/2017 |
| WO | 2018189502 A1 | 10/2018 |
| WO | 2018213641 A1 | 11/2018 |

OTHER PUBLICATIONS

Diffenbach (PCR methods and Applications (1993) vol. 3, pp. S30-S37) (Year: 1993).*
Roux et al (PCR Methods and Applications (1995) vol. 4, pp. s185-s194) (Year: 1995).*
Leach L. et al.,: "Development and validation of a real-time PCR assay for rapid detection of Candida auris from survellance samples", J. Clin. Microbiology, vol. 56, No. 2, Feb. 1, 2018 (Feb. 1, 2018), p. e01223-17.
Milena Kordalewska et al: "Rapid and Accurate Molecular Identification of the Emerging Multidrug-Resistant Pathogen Candida auris", Journal of Clinical Microbiology, vol. 55, No. 8, May 24, 2017 (May 24, 2017), pp. 2445-2452.
Wee Gyo Lee et al: "First Three Reported Cases of Nosocomial Fungemia Caused by Candida auris", Journal of Clinical Microbiology, vol. 49, No. 9, Jun. 29, 2011 (Jun. 29, 2011), pp. 3139-3142.
Theill Laura et al: "Single-tube classical PCR for Candida auris and Candida haemulonii identification", Revista Iberoamericana De Micologia, vol. 35, No. 2, Apr. 21, 2018 (Apr. 21, 2018) , pp. 110-112.
International Search Report and Written Opinion for PCT/EP2019/083389, mailed Feb. 17, 2020.
Ziauddin Khan et al., Increasing prevalence, molekular characterization and antifungal drug susceptibility of serial Candida auris Isolates in Kuweit, PLOS One, pp. 1-12, 2018.
Lee, W.G., et al., First Three Reported Cases of Nosocomial Fungemia Caused by Candida auris, Journal of Clinical Microbiology, Jun. 29, 2011, pp. 3139-3142, vol. 49, No. 9.
Chinese Office Action issued Jul. 28, 2023 in Application No. 201980079763.0, 10 pages.
Xia, Q., et al., Establishment of fluorescence quantitation PCR for the quantitative detection of five species of Candida, Laboratory Medicine, 2015, pp. 265-268, vol. 30, No. 3.

* cited by examiner

*Primary Examiner* — Katherine D Salmon
(74) *Attorney, Agent, or Firm* — Daniel E. Agnew (57) ABSTRACT

Methods for the rapid detection of the presence or absence of *Candida auris* (CA) in a biological or non-biological sample are described. The methods can include performing an amplifying step, a hybridizing step, and a detecting step. Furthermore, primers, probes targeting the CA 5.8s/ITS2 rRNA gene, along with kits are provided that are designed for the detection of CA.

16 Claims, 1 Drawing Sheet
Specification includes a Sequence Listing.

COMPOSITIONS AND METHODS FOR DETECTION OF *CANDIDA AURIS*

CROSS REFERENCE TO RELATED APPLICATIONS

This application is a U.S. national stage filing under 35 U.S.C. § 371 of International Application No. PCT/EP2019/083389, filed Dec. 3, 2019, entitled "COMPOSITIONS AND METHODS FOR DETECTION OF CANDIDA AURIS", which claims benefit of priority to U.S. Provisional Application Ser. No. 62/774,742, entitled "COMPOSITIONS AND METHODS FOR DETECTION OF CANDIDA AURIS", filed Dec. 3, 2018, the disclosure of each of which is incorporated herein by reference in its entirety.

REFERENCE TO SEQUENCE LISTING

This application contains a Sequence Listing submitted as an electronic text file named "35020_Sequence_Listing.txt", having a size in bytes of 4 kb, and created on Oct. 18, 2019.

FIELD OF THE INVENTION

The present disclosure relates to the field of molecular diagnostics, and more particularly to detection of *Candida auris*.

BACKGROUND OF THE INVENTION

*Candida auris* (*C. auris*, CA) is an emerging fungus that presents a serious global health threat. Although *C. auris* was first identified in 2009 in Japan, retrospective review of *Candida* strain collections found that the earliest known strain of *C. auris* dates to 1996 in South Korea. Although *C. auris* was just recognized in 2009, it has emerged quickly and has been reported from over 20 countries, including the United States. Healthcare facilities in several countries have reported that *C. auris* has been causing severe illness in hospitalized patients. In some patients, this yeast can enter the bloodstream and spread throughout the body, causing serious invasive infections.

*Candida auris* is a concern mainly for several reasons: 1) It is often multidrug-resistant, meaning that it is resistant to multiple antifungal drugs commonly used to treat *Candida* infections; 2) It is difficult to identify with standard laboratory methods, and it can be misidentified in labs without specific technology. Misidentification may lead to inappropriate management and 3) It has caused outbreaks in healthcare settings. For this reason, it is important to quickly identify *C. auris* in a hospitalized patient so that healthcare facilities can take special precautions to stop its spread.

Approximately 54% of *C. auris* cases have been identified from blood; the remaining 46% of cases were identified in other body sites, including, but not limited to, urine, wounds, sputum, and bile. Some clinical laboratories do not typically determine the species of isolates from non-sterile sites since presence of *Candida* in these sites may represent colonization rather than infection and would not require treatment. However, *C. auris* is important to identify even from a non-sterile body site because presence of *C. auris* in any body site can represent wider colonization, posing a risk for transmission and requiring implementation of infection control precautions.

Like other *Candida* infections, *C. auris* infections are usually diagnosed by culture of blood or other body fluids. However, *C. auris* is harder to identify from cultures than other, more common types of *Candida*. For example, it can be confused with other types of yeasts, particularly *Candida haemulonii*. Special laboratory tests are needed to identify *C. auris*.

Limited data suggest that the risk factors for *Candida auris* infections are generally similar to risk factors for other types of *Candida* infections. These risk factors include recent surgery, diabetes, broad-spectrum antibiotic and antifungal use.

Patients who have been hospitalized in a healthcare facility a long time, have lines and tubes that go into their body (such as breathing tubes, feeding tubes and central venous catheters), or have previously received antibiotics or antifungal medications, appear to be at highest risk of infection with *C. auris*. Infections have been found in patients of all ages, from preterm infants to the elderly. Further study is needed to learn more about risk factors for *C. auris* infection.

The appearance and color of *Candida auris* colonies in culture may aid in species identification, but cannot be used as the only identification method for *C. auris*, since *C. auris* cannot be distinguished from other more common species of *Candida* without using other methods. Diagnostic devices based on matrix-assisted laser desorption/ionization time-of-flight (MALDI-TOF) can differentiate *C. auris* from other *Candida* species, but not all the reference databases included in MALDI-TOF devices allow for detection. Thus there is a need in the art for a better and complete method to specifically detect *C. auris*.

SUMMARY OF THE INVENTION

Certain embodiments in the present disclosure relate to methods for the rapid detection of the presence or absence of *Candida auris* (CA) in a biological or non-biological sample, for example, multiplex detection of CA by real-time polymerase chain reaction in a single test tube. Embodiments include methods of detection of CA comprising performing at least one cycling step, which may include an amplifying step and a hybridizing step. Furthermore, embodiments include primers, probes, and kits that are designed for the detection of CA in a single tube. The detection methods are designed to target specific genes in the *Candida auris* genome with a potential to discriminate against the nearest neighbors *Candida haemulonii* and *Saccharomyces cerevisiae*.

A method for detecting *Candida auris* (CA) in a sample is provided, including performing an amplifying step including contacting the sample with a set of oligonucleotide primers designed to target a specific CA gene to produce an amplification product if CA is present in the sample; performing a hybridizing step including contacting the amplification product with one or more detectable oligonucleotide probes to the target CA gene; and detecting the presence or absence of the amplified product, wherein the presence of the amplified product is indicative of the presence of CA in the sample and wherein the absence of the amplified product is indicative of the absence of CA in the sample; wherein the target CA gene is the 5.8s/ITS2 rRNA gene.

In one aspect a method of detecting *Candida auris* (CA) in a sample is provided, the method comprising performing an amplifying step comprising contacting the sample with a set of CA 5.8s/ITS2 rRNA gene primers to produce an amplification product if CA nucleic acid is present in the sample; performing a hybridizing step comprising contacting the amplification product with one or more detectable 5.8s/ITS2 rRNA gene probes; and detecting the presence or absence of the amplification product, wherein the presence of the amplification product is indicative of the presence of CA in the sample and wherein the absence of the amplification product is indicative of the absence of CA in the sample; wherein the set of CA 5.8s/ITS2 rRNA gene primers comprises a first oligonucleotide primer comprising a first nucleic acid sequence selected from the group consisting of SEQ ID NOs: 1-3, or a complement thereof, and a second oligonucleotide primer comprising a second nucleic acid sequence selected from the group consisting of SEQ ID NOs: 5-6, and 8 or a complement thereof; and wherein the one or more detectable CA 5.8s/ITS2 rRNA gene oligonucleotide probe comprises a third nucleic acid sequence selected from the group consisting of SEQ ID NOs: 9-11, or the complement thereof.

In some embodiments the hybridizing step comprises contacting the amplification product with the detectable CA 5.8s/ITS2 rRNA gene probe that is labeled with a donor fluorescent moiety and a corresponding acceptor moiety; and the detecting step comprises detecting the presence or absence of fluorescence resonance energy transfer (FRET) between the donor fluorescent moiety and the acceptor moiety of the probe, wherein the presence or absence of fluorescence is indicative of the presence or absence of CA in the sample. In some embodiments the amplifying and the hybridizing steps are repeated. Herein, the number of repetitions depends, e.g., on the nature of the sample. If the sample is a complex mixture of nucleic acids, more amplifying and hybridizing steps will be required to amplify the target sequence sufficient for detection. In some embodiments, the amplifying and the hybridizing steps are repeated at least about 20 times, but may be repeated as many as at least 25, 30, 40, 50, 60, or even 100 times. Further, detecting the presence or absence of the amplification product may be performed during or after each amplifying and hybridizing step, during or after every other amplifying and hybridizing step, during or after particular amplifying and hybridizing steps or during or after particular amplifying and hybridizing steps, in which—if present—sufficient amplification product for detection is expected. In some embodiments, the amplifying step employs a polymerase enzyme having 5' to 3' nuclease activity. In some embodiments, the donor fluorescent moiety and the corresponding acceptor moiety are within no more than 8-20 nucleotides of each other on the probe. In some embodiments, the acceptor moiety is a quencher. In some embodiments the oligonucleotides comprise or consist of a sequence of nucleotides selected from SEQ ID NOs: 1-3, 5-6, 8, 9-11, or a complement thereof have 100 or fewer nucleotides, 50 or fewer nucleotides, 40 or fewer nucleotides or 30 or fewer nucleotides. In some embodiments, the first and second CA 5.8s/ITS2 rRNA gene primers and detectable CA 5.8s/ITS2 rRNA probe have 40 or fewer nucleotides (e.g. 35 or fewer nucleotides, 30 or fewer nucleotides, etc.). In some embodiments, the first oligonucleotide primer comprises or consists of a nucleic acid sequence of SEQ ID NO: 2, the second oligonucleotide primer comprises or consists of a nucleic acid sequence of SEQ ID NO: 5, and the oligonucleotide probe comprises or consists of a nucleic acid sequence of SEQ ID NO: 10. In certain embodiments, either one of the first, second, and third oligonucleotides have 40 or fewer nucleotides. In some embodiments, at least one of the first, second, and third oligonucleotides comprises at least one modified nucleotide.

In another embodiment, the present disclosure provides an oligonucleotide that includes a nucleic acid having at least 70% sequence identity (e.g., at least 75%, 80%, 85%, 90% or 95%, etc.) to one of SEQ ID NOs: 1-3, 5-6, 8, 9-11, or a complement thereof, which oligonucleotide has 100 or fewer nucleotides. Generally, these oligonucleotides may be primer nucleic acids, probe nucleic acids, or the like in these embodiments. In some embodiments, the oligonucleotides comprise at least one modified nucleotide, e.g., to alter nucleic acid hybridization stability relative to unmodified nucleotides. Optionally, the oligonucleotides comprise at least one label and/or at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. In some embodiments, at least one of the first and second target CA gene primers and detectable target CA gene probe comprises at least one modified nucleotide.

In some embodiments, amplification (the amplifying step) can employ a polymerase enzyme having 5' to 3' nuclease activity. Thus, the donor fluorescent moiety and the acceptor moiety, e.g., a quencher, may be within no more than 5 to 20 nucleotides (e.g., 8 or 10) of each other along the length of the probe. In another aspect, the detectable probe includes a nucleic acid sequence that permits secondary structure formation. Such secondary structure formation generally results in spatial proximity between the first and second fluorescent moiety. According to this method, the second fluorescent moiety on the probe can be a quencher.

The present disclosure provides for methods of detecting the presence or absence of CA in a biological sample from an individual. Such methods generally include performing at least one cycling step, which includes an amplifying step and a dye-binding step. Typically, the amplifying step includes contacting the sample with a plurality of pairs of primers designed to target a specific CA gene to produce one or more target CA gene amplification products if the target CA gene nucleic acid molecule is present in the sample, and the dye-binding step includes contacting the target CA gene amplification product with a double-stranded DNA binding dye. In one embodiment, the target CA gene is the CA 5.8s/ITS2 rRNA gene. Such methods also include detecting the presence or absence of binding of the double-stranded DNA binding dye into the amplification product, wherein the presence of binding is indicative of the presence of CA in the sample, and wherein the absence of binding is indicative of the absence of CA in the sample. A representative double-stranded DNA binding dye is ethidium bromide. In addition, such methods also can include determining the melting temperature between the target CA gene amplification product and the double-stranded DNA binding dye, wherein the melting temperature confirms the presence or absence of CA.

In yet another aspect, a kit for detecting the CA 5.8s/ITS2 rRNA gene is provided. The kit can include one or more sets of primers specific for amplification of the CA 5.8s/ITS2 rRNA gene and one or more detectable probes specific for detection of the CA 5.8s/ITS2 rRNA gene amplification products.

In particular, the oligonucleotide primers and probes disclosed above in connection with the method according to the invention are suitable to being included in a kit according to the invention. Herein, a kit for detecting the 5.8s/ITS2 rRNA gene of *Candida auris* (CA) is provided comprising a first oligonucleotide primer comprising a first nucleic acid sequence selected from the group consisting of SEQ ID NOs: 1-3, or a complement thereof; a second oligonucleotide primer comprising a second nucleic acid sequence selected from the group consisting of SEQ ID NOs: 5-6, and 8 or a complement thereof; and a fluorescently detectably labeled oligonucleotide probe comprising a third nucleic acid sequence selected from the group consisting of SEQ ID NOs: 9-11, or a complement thereof, the detectably labeled probe configured to hybridize to an amplicon generated by the first and the second oligonucleotide primer. In one aspect, the kit can include probes already labeled with donor and corresponding acceptor moiety, e.g., another fluorescent moiety or a dark quencher, or can include fluorophoric moieties for labeling the probes. The kit can also include at least one of nucleoside triphosphates, nucleic acid polymerase, and buffers necessary for the function of the nucleic acid polymerase. The kit can also include a package insert and instructions for using the primers, probes, and fluorophoric moieties to detect the presence or absence of CA in a sample. In some embodiments, the third detectably labeled oligonucleotide probe comprises a donor fluorescent moiety and a corresponding acceptor moiety. In some embodiments, the acceptor moiety is a quencher. In some embodiments, the first oligonucleotide primer comprises or consists of a nucleic acid sequence of SEQ ID NO: 2, the second oligonucleotide primer comprises or consists of a nucleic acid sequence of SEQ ID NO: 5, and the oligonucleotide probe comprises or consists of a nucleic acid sequence of SEQ ID NO: 10. In certain embodiments, either one of the first, second, and third oligonucleotides have 40 or fewer nucleotides. In some embodiments, at least one of the first, second, and third oligonucleotides comprises at least one modified nucleotide. In some embodiments, the first, second, and third oligonucleotides have 40 or fewer nucleotides.

In another aspect, compositions are provided comprising a set of oligonucleotide primers for amplifying a target CA gene as disclosed above. In some embodiments, the set of CA 5.8s/ITS2 rRNA gene primers comprises a first primer comprising or consisting of a first oligonucleotide sequence selected from the group consisting of SEQ ID NOs: 1-3 or a complement thereof, and a second primer comprising or consisting of a second oligonucleotide sequence selected from the group consisting of SEQ ID NOs: 5-6, and 8, or a complement thereof. In certain embodiments the composition further comprises one or more detectable CA 5.8s/ITS2 rRNA gene probes that comprises or consists of a third oligonucleotide sequence selected from the group consisting of SEQ ID NOs: 9-11, or the complement thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Diagnosis of CA infection by nucleic acid amplification provides a method for rapidly and accurately detecting the fungal infection. A real-time assay for detecting CA in a sample is described herein. Primers and probes for detecting CA are provided, as are articles of manufacture or kits containing such primers and probes. The increased sensitivity of real-time PCR for detection of CA compared to other methods, as well as the improved features of real-time PCR including sample containment and real-time detection of the amplified product, make feasible the implementation of this technology for routine diagnosis of CA infections in the clinical laboratory.

The present disclosure includes oligonucleotide primers and fluorescent labeled hydrolysis probes that hybridize to a specific gene locus of the CA genome in order to specifically identify CA using TaqMan® amplification and detection technology. Target selection for CA required a comprehensive search of the public sequence database, as well as literature search for CA targets with a potential to discriminate against the nearest neighbors *Candida haemulonii* and *Saccharomyces cerevisiae*. Multiple targets from the public sequence database were analyzed in the target selection process but many showed cross reactivity with *C. haemulonii* and *S. cerevisiae*. Furthermore, sequences in the public database are complicated by "bulk" sequence data from multicopy targets. As a result of the analysis, a target CA gene that was chosen was the CA 5.8s/ITS2 rRNA gene (GenBank accession number AB375772).

The disclosed methods may include performing at least one cycling step that includes amplifying one or more portions of the nucleic acid molecule gene target from a sample using one or more pairs of primers. "Primer(s)" as used herein refer to oligonucleotide primers that specifically anneal to the target gene in CA, and initiate DNA synthesis therefrom under appropriate conditions producing the respective amplification products. Each of the discussed primers anneals to a target within or adjacent to the respective target nucleic acid molecule such that at least a portion of each amplification product contains nucleic acid sequence corresponding to the target. The one or more amplification products are produced provided that one or more of the target CA gene nucleic acid is present in the sample, thus the presence of the one or more of target CA gene amplification products is indicative of the presence of CA in the sample. The amplification product should contain the nucleic acid sequences that are complementary to one or more detectable probes for target CA gene. "Probe(s)" as used herein refer to oligonucleotide probes that specifically anneal to nucleic acid sequence encoding the target CA gene. Each cycling step includes an amplification step, a hybridization step, and a detection step, in which the sample is contacted with the one or more detectable probes for detection of the presence or absence of CA in the sample.

As used herein, the term "amplifying" refers to the process of synthesizing nucleic acid molecules that are complementary to one or both strands of a template nucleic acid molecule. Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

Detection of CA

The present disclosure provides methods to detect CA by amplifying, for example, a portion of the CA 5.8s/ITS2 rRNA gene nucleic acid sequence. Nucleic acid sequences of the gene are publicly available (e.g., GenBank Accession No. AB375772). Specifically, primers and probes to amplify and detect specific CA nucleic acid molecule targets are provided by the embodiments in the present disclosure.

For detection of CA, primers and probes to amplify the CA 5.8s/ITS2 rRNA gene are provided. Nucleic acids other than those exemplified herein can also be used to detect CA in a sample. For example, functional variants can be evaluated for specificity and/or sensitivity by those of skill in the art using routine methods. Representative functional variants can include, e.g., one or more deletions, insertions, and/or substitutions in the target CA gene nucleic acids disclosed herein.

More specifically, embodiments of the oligonucleotides each include a nucleic acid with a sequence selected from SEQ ID NOs: 1-12, a substantially identical variant thereof in which the variant has at least, e.g., 80%, 90%, or 95% sequence identity to one of SEQ ID NOs: 1-12, or a complement of SEQ ID NOs: 1-12 and the variant.

TABLE I 5.8s/ITS2 rRNA Primers
Forward and Reverse Primers

| Oligo Name | SEQ ID NO: | Sequence |
|---|---|---|
| CAUR001 | 1 | TGAGCGTGATGTCTTCTCAC |
| CAUR003 | 2 | GAGCGTGATGTCTTCTCACC |
| CAUR005 | 3 | ACTGATTTGGATTTTAAAACTAACCCAA |
| CAUR007 | 4 | AACTAACCCAACGTTAAGTTCAAC |
| CAUR002 | 5 | CCTGATTTGAGGCGACAACAA |
| CAUR004 | 6 | CGTCTGCAAGTCATACTACGTA |
| CAUR006 | 7 | CGATGATTCACGTCTGCAAGTC |
| CAUR008 | 8 | CAACGCCACCGCGAA | substitutions such as one or more nucleotide additions, deletions or substitutions at the 5' end and/or the 3' end of the respective sequence of SEQ ID NOs: 1-12. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-deazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the target CA 5.8s/ITS2 rRNA gene can be designed using, for example, a computer program such as OLIGO (Molecular Biology Insights Inc., Cascade, Colo.).

TABLE II 5.8s/ITS2 rRNA Probes
Probes

| Oligo Name | SEQ ID NO: | Sequence | Modifications |
|---|---|---|---|
| CAUR101HQ6 | 9 | <H>CTTCGC<Q>GGTGGCGTTGCATTCACA<Phos> | H = HEX_Thr, Q = BHQ2, Phos = phosphate |
| CAUR103HQ6 | 10 | <H>TTCGCG<Q>GTGGCGTTGCATTCACA<Phos> | H = HEX_Thr, Q = BHQ2, Phos = phosphate |
| CAUR105HQ10 | 11 | <H>ACAACGGATC<Q>TCTTGGTTCTCGCATCGATG<Phos> | H = HEX_Thr, Q = BHQ2, Phos = phosphate |
| CAUR107HQ8 | 12 | <H>CTCGCATC<Q>GATGAAGAACGCAGCGAAA<Phos> | H = HEX_Thr, Q = BHQ2, Phos = phosphate |

In one embodiment, the above described sets of primers and probes are used in order to provide for detection of CA in a biological sample suspected of containing CA. The sets of primers and probes may comprise or consist of the primers and probes specific for the nucleic acid sequences of the CA 5.8s/ITS2 rRNA gene comprising or consisting of the nucleic acid sequences of SEQ ID NOs: 1-12. In another embodiment, the primers and probes for the CA 5.8s/ITS2 rRNA genes comprise or consist of a functionally active variant of any of the primers and probes of SEQ ID NOs: 1-12.

A functionally active variant of any of the primers and/or probes of SEQ ID NOs: 1-12 may be identified by using the primers and/or probes in the disclosed methods. A functionally active variant of a primer and/or probe of any of the SEQ ID NOs: 1-12 pertains to a primer and/or probe which provide a similar or higher specificity and sensitivity in the described method or kit as compared to the respective sequence of SEQ ID NOs: 1-12.

The variant may, e.g., vary from the sequence of SEQ ID NOs: 1-12 by one or more nucleotide additions, deletions or Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length). In some embodiments oligonucleotide primers are 40 or fewer nucleotides in length.

In addition to a set of primers, the methods may use one or more probes in order to detect the presence or absence of CA. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a target CA gene nucleic acid. A "probe"

can be referred to as a "detection probe" meaning that it detects the target nucleic acid.

In some embodiments, the described CA 5.8s/ITS2 rRNA gene probes can be labeled with at least one fluorescent label. In one embodiment, the CA 5.8s/ITS2 rRNA gene probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs: 9-12.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of CA 5.8s/ITS2 rRNA gene primers and probes nucleic acid molecules. Constructs can be used, for example, as control template nucleic acid molecules. Vectors suitable for use are commercially available and/or produced by recombinant nucleic acid technology methods routine in the art. CA 5.8s/ITS2 rRNA gene nucleic acid molecules can be obtained, for example, by chemical synthesis, direct cloning from CA, or by PCR amplification.

Constructs suitable for use in the methods typically include, in addition to the CA 5.8s/ITS2 rRNA gene nucleic acid molecules (e.g., a nucleic acid molecule that contains one or more sequences of SEQ ID NOs: 1-12), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing target CA gene nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described target CA gene nucleic acid sequences (e.g., SEQ ID NOs: 1-7). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described target CA gene nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ nucleic acid such as RNA or DNA (cDNA). The template nucleic acid need not be purified; it may be a minor fraction of a complex mixture, such as nucleic acid contained in human cells. Nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, protozoa viruses, organelles, or higher organisms such as plants or animals.

The oligonucleotide primers are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg protodenatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety and a corresponding quencher, which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced there between.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescence emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, VA)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of CA

The present disclosure provides methods for detecting the presence or absence of CA in a biological or non-biological sample. Methods provided avoid problems of sample contamination, false negatives, and false positives. The methods include performing at least one cycling step that includes amplifying a portion of target nucleic acid molecules from a sample using one or more pairs of primers, and a FRET detecting step. Multiple cycling steps are performed, preferably in a thermocycler. Methods can be performed using the primers and probes to detect the presence of CA, and the detection of the target CA gene indicates the presence of CA in the sample.

As described herein, amplification products can be detected using labeled hybridization probes that take advantage of FRET technology. One FRET format utilizes TaqMan® technology to detect the presence or absence of an amplification product, and hence, the presence or absence of CA. TaqMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of CA in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of CA genomes). If amplification of target nucleic acid occurs and an amplification product is produced, the step of hybridizing results in a detectable signal based upon FRET between the members of the pair of probes.

Generally, the presence of FRET indicates the presence of CA in the sample, and the absence of FRET indicates the absence of CA in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of a CA infection.

Representative biological samples that can be used in practicing the methods include, but are not limited to respiratory specimens, fecal specimens, blood specimens, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release CA nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the probes from the amplification products can confirm the presence or absence of CA in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product. It is understood that the embodiments of the present disclosure are not limited by the configuration of one or more commercially available instruments.

Articles of Manufacture/Kits

Embodiments of the present disclosure further provide for articles of manufacture, compositions or kits to detect CA. An article of manufacture can include primers and probes used to detect the target CA gene, together with suitable packaging materials. Compositions can include primers used to amplify the target CA gene. In certain embodiments compositions can also comprise probes for detecting the target CA gene. Representative primers and probes for detection of CA are capable of hybridizing to target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the probes. Examples of suitable FRET donor fluorescent moieties and corresponding acceptor fluorescent moieties are provided above.

Articles of manufacture can also contain a package insert or package label having instructions thereon for using the primers and probes to detect CA in a sample. Articles of manufacture and compositions may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples, tables and figures are provided to aid the understanding of the subject matter, the true scope of which is set forth in the appended claims. It is understood that modifications can be made in the procedures set forth without departing from the spirit of the invention.

Example 1

Target selection for CA was the result of a comprehensive search of the public sequence database, as well as a literature search for CA targets with a potential to discriminate against the nearest neighbors, *Candida haemulonii* and *Saccharomyces cerevisiae*. Multiple targets from the public sequence database were analyzed in the target selection process of the design phase, but all showed cross reactivity with *C. haemulonii* and *S. cerevisiae*. The sequences in the public database are complicated by "bulk" sequence data from multicopy targets. BLAST analysis of the chosen oligonucleotides indicated that the only significant cross reactivity will be with *Candida haemulonii*.

Real-time PCR detection of CA were performed using either the Cobas® 4800 system or the Cobas® 6800/8800 systems platforms (Roche Molecular Systems, Inc., Pleasanton, CA). The final concentrations of the amplification reagents are shown below:

TABLE III

| PCR Amplification Reagents | |
|---|---|
| Master Mix Component | Final Conc (50 uL) |
| DMSO | 0-5.4 % |
| NaN3 | 0.027-0.030 % |
| Potassium acetate | 120.0 mM |
| Glycerol | 3.0 % |
| Tween 20 | 0.02 % |
| EDTA | 0-43.9 uM |
| Tricine | 60.0 mM |
| Aptamer | 0.18-0.22 uM |
| UNG Enzyme | 5.0-10.0 U |
| Z05-SP-PZ Polymerase | 30.0-45.0 U |
| dATP | 400.0-521.70 uM |
| dCTP | 400.0-521.70 uM |
| dGTP | 400.0-521.70 uM |
| dUTP | 800.0-1043.40 uM |
| Forward primer oligonucleotides | 0.15-0.50 µM |
| Reverse primer oligonucleotides | 0.15-0.50 µM |
| Probe oligonucleotides | 0.10 µM |
| Manganese Acetate | 3.30-3.80 mM |

The following table shows the typical thermoprofile used for PCR amplification reaction:

TABLE IV

PCR Thermoprofile

| Program Name | Target (° C.) | Acquisition Mode | Hold (hh:mm:ss) | Ramp Rate (° C./s) | Cycles | Analysis Mode |
|---|---|---|---|---|---|---|
| Pre-PCR | 50 | None | 00:02:00 | 4.4 | 1 | None |
| | 94 | None | 00:00:05 | 4.4 | | |
| | 55 | None | 00:02:00 | 2.2 | | |
| | 60 | None | 00:06:00 | 4.4 | | |
| | 65 | None | 00:04:00 | 4.4 | | |
| 1st Measurement | 95 | None | 00:00:05 | 4.4 | 5 | Quantification |
| | 55 | Single | 00:00:30 | 2.2 | | |
| 2nd Measurement | 91 | None | 00:00:05 | 4.4 | 45 | Quantification |
| | 58 | Single | 00:00:25 | 2.2 | | |
| Cooling | 40 | None | 00:02:00 | 2.2 | 1 | None |

The Pre-PCR program comprised initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription. PCR cycling was divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

The amplification and detection of the CA 5.8s/ITS2 rRNA gene were performed using the conditions described above. The results of the experiments using several selected oligonucleotide primers and probes against genomic CA DNA present at a concentration of 100,000, 10,000 and 1,000 genomic equivalent per PCR reaction (ge/PCR) and genomic *Candida auris* (CA) and *Candida haemulonii*, (CH) both at concentrations of 100,000 genomic equivalent per PCR reaction (ge/PCR) are shown below as Ct values (threshold cycle) for the amplification reactions.

TABLE V

Amplification and Detection of CA 5.8 s/ITS2 rRNA gene

| Assay No. | Forward primer SEQ ID NO | Reverse primer SEQ ID NO | Probe SEQ ID NO | Organism | Input copy | Ct Value |
|---|---|---|---|---|---|---|
| AUR1 | 1 | 5 | 9 | CA | 100,000 ge/PCR | 16.6 |
| | | | | CH | 100,000 ge/PCR | ND |
| AUR2 | 2 | 5 | 10 | CA | 100,000 ge/PCR | 16.7 |
| | | | | CH | 100,000 ge/PCR | ND |
| AUR3 | 3 | 6 | 11 | CA | 100,000 ge/PCR | 29.5 |
| | | | | CH | 100,000 ge/PCR | ND |
| AUR4 | 4 | 7 | 12 | CA | 100,000 ge/PCR | 17.8 |
| | | | | CH | 100,000 ge/PCR | 26.7 |
| AUR5 | 3 | 8 | 11 | CA | 100,000 ge/PCR | 17.1 |
| | | | | CH | 100,000 ge/PCR | ND |
| AUR6 | 3 | 7 | 11 | CA | 100,000 ge/PCR | 17.6 |
| | | | | CH | 100,000 ge/PCR | 35.9 |

Figure 1:
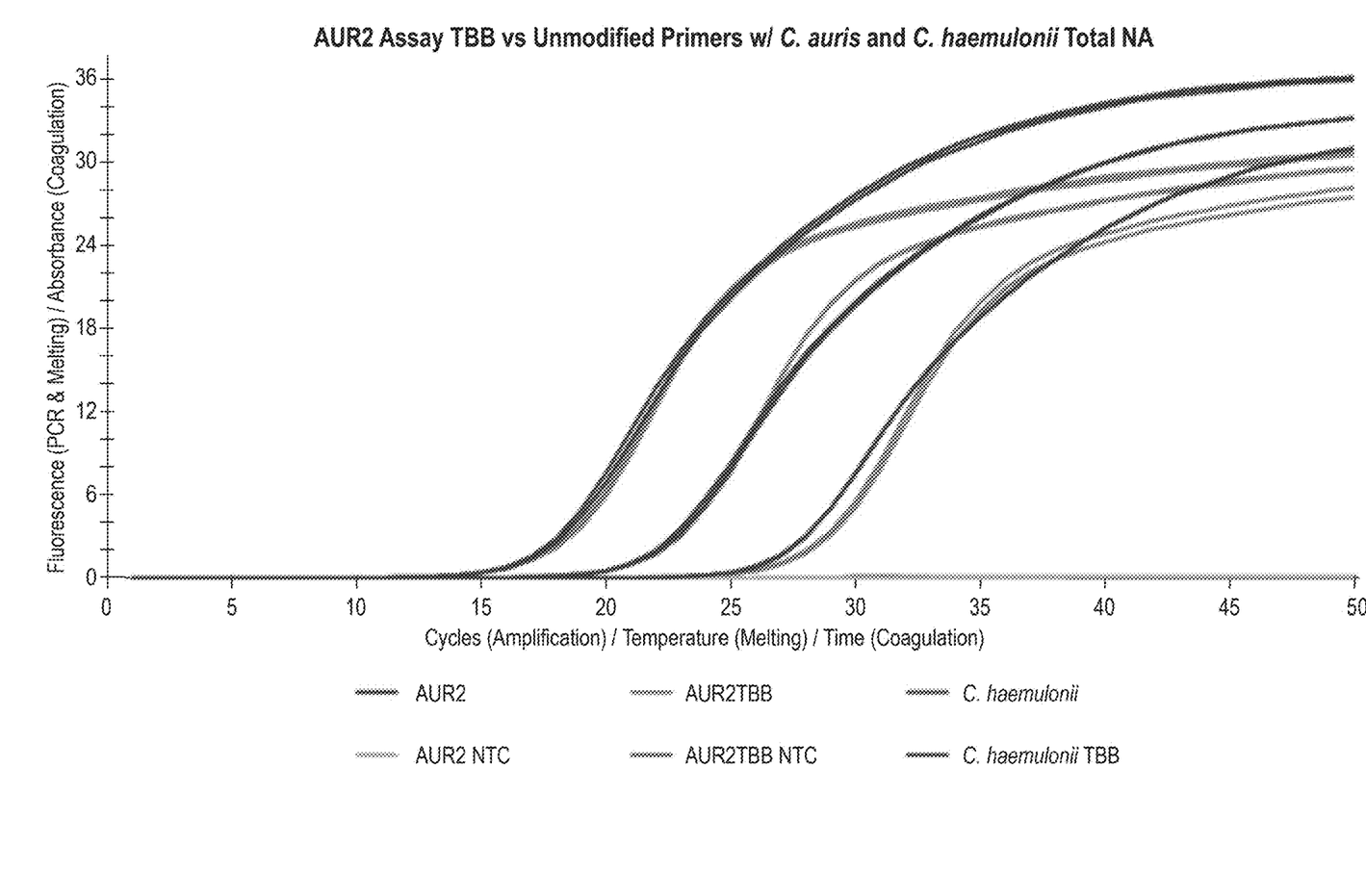
FIG. 1 shows PCR growth curves of the real-time PCR experiment generated from CA 5.8s/ITS2 rRNA primers (SEQ ID Nos: 2 and 5) and probe (SEQ ID NO: 10) in the AUR2 assay (see Table V) in the presence of genomic *C. auris* DNA template at concentrations of 100,000, 10,000 and 1,000 genomic equivalent concentrations per PCR reaction (ge/PCR), and in the presence of 100,000 ge/PCR genomic *C. haemulonii* template or with no template DNA (NTC). TBB refers to primers modified with a tert-butylbenzyl moiety at the 3' terminus.

The assays that exhibited the best sensitivity for CA and best exclusivity against CH were AUR1, AUR2 and AUR5 while the AUR4 and AUR 6 assays showed some cross-reactivity against CH. The AUR2 assay (i.e. Forward primer SEQ ID NO: 2, Reverse primer SEQ ID NO: 5 and Probe SEQ ID NO: 10) was further tested in genomic CA DNA present at concentrations of 100,000, 10,000 and 1,000 ge/PCR and in genomic CH DNA present at a concentration of 100,000 ge/PCR and the PCR growth curves of this experiment are shown in FIG. 1. No difference was observed in the growth curves between unmodified primers (AUR2) and primers modified with a tert-butyl-benzyl moiety at the 3' terminus (AUR2TBB). No signals were detected for the CH templates using modified or unmodified primers (*C. haemulonii/C. haemulonii* TBB) and for the No Template Controls (AUR2 NTC/AUR2TBB NTC).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

| INFORMAL SEQUENCE LISTING | | |
|---|---|---|
| SEQ ID NO 1: | CAUR001 forward primer | TGAGCGTGATGTCTTCTCAC |
| SEQ ID NO 2: | CAUR003 forward primer | GAGCGTGATGTCTTCTCACC |
| SEQ ID NO 3: | CAUR005 forward primer | ACTGATTTGGATTTTAAAACTAACCCAA |
| SEQ ID NO 4 | CAUR007 forward primer | AACTAACCCAACGTTAAGTTCAAC |
| SEQ ID NO 5: | CAUR002 reverse primer | CCTGATTTGAGGCGACAACAA |
| SEQ ID NO 6: | CAUR004 reverse primer | CGTCTGCAAGTCATACTACGTA |
| SEQ ID NO 7: | CAUR006 reverse primer | CGATGATTCACGTCTGCAAGTC |
| SEQ ID NO 8: | CAUR008 reverse primer | CAACGCCACCGCGAA |
| SEQ ID NO 9: | CAUR101HQ6 probe | CTTCGCGGTGGCGTTGCATTCACA |
| SEQ ID NO 10: | CAUR103HQ6 probe | TTCGCGGTGGCGTTGCATTCACA |

INFORMAL SEQUENCE LISTING

SEQ ID NO 11: CAUR105HQ10 probe     ACAACGGATCTCTTGGTTCTCGCATCGATG

SEQ ID NO 12: CAUR107HQ8 probe      CTCGCATCGATGAAGAACGCAGCGAAA

The invention claimed is:

1. A method of detecting *Candida auris* (CA) in a sample that discriminates against *Candida haemulonii*, the method comprising:
performing an amplifying step comprising contacting the sample with a set of CA 5.8s/ITS2 rRNA gene primers to produce an amplification product if CA 5.8s/ITS2 rRNA nucleic acid is present in the sample;
performing a hybridizing step comprising contacting the amplification product with one or more detectable CA 5.8s/ITS2 rRNA gene probes; and
detecting the presence or absence of the amplification product, wherein the presence of the amplification product is indicative of the presence of CA in the sample and wherein the absence of the amplification product is indicative of the absence of CA in the sample;
wherein the set of CA 5.8s/ITS2 rRNA gene primers comprises a first oligonucleotide primer comprising a first nucleic acid sequence selected from the group consisting of SEQ ID NOs: 1-3, and a second oligonucleotide primer comprising a second nucleic acid sequence selected from the group consisting of SEQ ID NOs: 5-6, and 8; and
wherein the one or more detectable CA 5.8s/ITS2 rRNA gene oligonucleotide probe comprises a third nucleic acid sequence selected from the group consisting of SEQ ID NOs: 9-11, or the complement thereof, and
wherein the combination of the first oligonucleotide primer, the second oligonucleotide primer and the detectably labeled probe exhibit no detectable cross-reactivity with *Candida haemulonii* in a PCR amplification reaction.

2. The method of claim 1, wherein the hybridizing step comprises contacting the amplification product with the detectable CA 5.8s/ITS2 rRNA gene oligonucleotide probe that is labeled with a donor fluorescent moiety and a corresponding acceptor moiety; and the detecting step comprises detecting the presence or absence of fluorescence resonance energy transfer (FRET) between the donor fluorescent moiety and the acceptor moiety of the oligonucleotide probe, wherein the presence or absence of fluorescence is indicative of the presence or absence of CA in the sample.

3. The method of claim 1, wherein said amplifying step employs a polymerase enzyme having 5' to 3' nuclease activity.

4. The method of claim 2, wherein the donor fluorescent moiety and the corresponding acceptor moiety are within no more than 8-20 nucleotides of each other on the probe.

5. The method of claim 2, wherein the acceptor moiety is a quencher.

6. The method of claim 1, wherein the first oligonucleotide primer comprises a nucleic acid sequence of SEQ ID NO: 2, the second oligonucleotide primer comprises a nucleic acid sequence of SEQ ID NO: 5, and the oligonucleotide probe comprises a nucleic acid sequence of SEQ ID NO: 10.

7. The method of claim 1, wherein the first, second, and third oligonucleotides have 40 or fewer nucleotides.

8. The method of claim 1, wherein at least one of the first, second, and third oligonucleotides comprises at least one modified nucleotide.

9. A kit for detecting a nucleic acid of *Candida auris* (CA) that discriminates against *Candida haemulonii*, the kit comprising:
   a first oligonucleotide primer comprising a first nucleic acid sequence selected from the group consisting of SEQ ID NOs: 1-3;
   a second oligonucleotide primer comprising a second nucleic acid sequence selected from the group consisting of SEQ ID NOs: 5-6, and 8; and
   a fluorescently detectably labeled oligonucleotide probe comprising a third nucleic acid sequence selected from the group consisting of SEQ ID NOs: 9-11, or a complement thereof, the detectably labeled probe configured to hybridize to an amplicon generated by the first and the second oligonucleotide primer,
   wherein the combination of the first oligonucleotide primer, the second oligonucleotide primer and the detectably labeled probe exhibit no detectable cross-reactivity with *Candida haemulonii* in a PCR amplification reaction.

10. The kit of claim 9, wherein the third detectably labeled oligonucleotide probe comprises a donor fluorescent moiety and a corresponding acceptor moiety.

11. The kit of claim 10, wherein the acceptor moiety is a quencher.

12. The kit of claim 9, further comprising at least one of nucleoside triphosphates, nucleic acid polymerase, and buffers necessary for the function of the nucleic acid polymerase.

13. The kit of claim 9, wherein at least one of the first, second, and third oligonucleotides comprises at least one modified nucleotide.

14. The kit of claim 9, wherein the first, second, and third oligonucleotides have 40 or fewer nucleotides.

15. The kit of claim 9, wherein the first oligonucleotide primer comprises a nucleic acid sequence of SEQ ID NO: 2, the second oligonucleotide primer comprises a nucleic acid sequence of SEQ ID NO: 5, and the oligonucleotide probe comprises a nucleic acid sequence of SEQ ID NO: 10.

16. The kit of claim 9, wherein cross-reactivity with *Candida haemulonii* is not detected at a concentration of up to 100,000 genomic equivalent per PCR reaction.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: CAUR001 forward primer

<400> SEQUENCE: 1
tgagcgtgat gtcttctcac                                            20

<210> SEQ ID NO 2
<211> LENGTH: 20
<212> TYPE: DNA
<213> ORGANISM: Artificial Sequence
<220> FEATURE:
<223> OTHER INFORMATION: CAUR003 forward primer

<400> SEQUENCE: 2
gagcgtgatg tcttctcacc                                            20

<210> SEQ ID NO 3
<211> LENGTH: 28
<212> TYPE: DNA
<213> ORGANISM: Artificial Sequence
<220> FEATURE:
<223> OTHER INFORMATION: CAUR005 forward primer

<400> SEQUENCE: 3
actgatttgg attttaaaac taacccaa                                   28

<210> SEQ ID NO 4
<211> LENGTH: 24
<212> TYPE: DNA
<213> ORGANISM: Artificial Sequence
<220> FEATURE:
<223> OTHER INFORMATION: CAUR007 forward primer

<400> SEQUENCE: 4
aactaaccca acgttaagtt caac                                       24

<210> SEQ ID NO 5
<211> LENGTH: 21
<212> TYPE: DNA
<213> ORGANISM: Artificial Sequence
<220> FEATURE:
<223> OTHER INFORMATION: CAUR002 reverse primer

<400> SEQUENCE: 5
cctgatttga ggcgacaaca a                                          21

<210> SEQ ID NO 6
<211> LENGTH: 22
<212> TYPE: DNA
<213> ORGANISM: Artificial Sequence

```
<220> FEATURE:
<223> OTHER INFORMATION: CAUR004 reverse primer

<400> SEQUENCE: 6
cgtctgcaag tcatactacg ta                                            22

<210> SEQ ID NO 7
<211> LENGTH: 22
<212> TYPE: DNA
<213> ORGANISM: Artificial Sequence
<220> FEATURE:
<223> OTHER INFORMATION: CAUR006 reverse primer

<400> SEQUENCE: 7
cgatgattca cgtctgcaag tc                                            22

<210> SEQ ID NO 8
<211> LENGTH: 15
<212> TYPE: DNA
<213> ORGANISM: Artificial Sequence
<220> FEATURE:
<223> OTHER INFORMATION: CAUR008 reverse primer

<400> SEQUENCE: 8
caacgccacc gcgaa                                                    15

<210> SEQ ID NO 9
<211> LENGTH: 24
<212> TYPE: DNA
<213> ORGANISM: Artificial Sequence
<220> FEATURE:
<223> OTHER INFORMATION: CAUR101HQ6 probe
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 9
cttcgcggtg gcgttgcatt caca                                          24

<210> SEQ ID NO 10
<211> LENGTH: 23
<212> TYPE: DNA
<213> ORGANISM: Artificial Sequence
<220> FEATURE:
<223> OTHER INFORMATION: CAUR103HQ6 probe
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' phosphate
<220> FEATURE:
<221> NAME/KEY: misc_feature
<222> LOCATION: (6)..(7)
<223> OTHER INFORMATION: BHQ-2

<400> SEQUENCE: 10
ttcgcggtgg cgttgcattc aca                                           23

<210> SEQ ID NO 11
<211> LENGTH: 30
<212> TYPE: DNA
```

```
<213> ORGANISM: Artificial Sequence
<220> FEATURE:
<223> OTHER INFORMATION: CAUR105HQ10 probe
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' phosphate
<220> FEATURE:
<221> NAME/KEY: misc_feature
<222> LOCATION: (10)..(11)
<223> OTHER INFORMATION: BHQ-2

<400> SEQUENCE: 11
acaacggatc tcttggttct cgcatcgatg                                    30

<210> SEQ ID NO 12
<211> LENGTH: 27
<212> TYPE: DNA
<213> ORGANISM: Artificial Sequence
<220> FEATURE:
<223> OTHER INFORMATION: CAUR107HQ8 probe
<220> FEATURE:
<221> NAME/KEY: misc_feature
<223> OTHER INFORMATION: 5' HEX-Thr
<220> FEATURE:
<221> NAME/KEY: misc_feature
<223> OTHER INFORMATION: 3' phosphate
<220> FEATURE:
<221> NAME/KEY: misc_feature
<222> LOCATION: (8)..(9)
<223> OTHER INFORMATION: BHQ-2

<400> SEQUENCE: 12
ctcgcatcga tgaagaacgc agcgaaa                                       27
```